(12) United States Patent
Green

(10) Patent No.: US 6,198,957 B1
(45) Date of Patent: Mar. 6, 2001

(54) RADIOTHERAPY MACHINE INCLUDING MAGNETIC RESONANCE IMAGING SYSTEM

(75) Inventor: Michael Curzon Green, Palo Alto, CA (US)

(73) Assignees: Varian, Inc.; Varian Medical Systems, Inc., both of Palo Alto, CA (US)

( * ) Notice: Subject to any disclaimer, the term of this patent is extended or adjusted under 35 U.S.C. 154(b) by 0 days.

(21) Appl. No.: 08/994,851

(22) Filed: Dec. 19, 1997

(51) Int. Cl.[7] .................................................. A61B 5/055
(52) U.S. Cl. .............................. 600/411; 600/422; 600/1; 378/65
(58) Field of Search ........................ 378/63, 65; 600/411, 600/415, 421, 422, 1, 2

(56) References Cited

U.S. PATENT DOCUMENTS

| | | | |
|---|---|---|---|
| 3,969,629 | 7/1976 | McIntyre | 250/503 |
| 4,791,371 * | 12/1988 | Krol | 600/422 |
| 4,805,626 * | 2/1989 | DiMassimo et al. | 600/422 |
| 4,875,487 | 10/1989 | Seppi | 128/660.03 |
| 4,998,268 * | 3/1991 | Winter | 378/63 |
| 5,107,839 * | 4/1992 | Houdek et al. | 600/411 |
| 5,178,146 * | 1/1993 | Giese | 600/411 |
| 5,327,884 * | 7/1994 | Hardy et al. | 600/411 |
| 5,357,958 | 10/1994 | Kaufman | 128/653.2 |
| 5,357,959 | 10/1994 | Fishman | 128/653.2 |
| 5,490,513 * | 2/1996 | Damadian et al. | 600/422 |
| 5,519,321 * | 5/1996 | Hagen et al. | 600/422 |
| 5,647,361 * | 7/1997 | Damadian | 600/411 |
| 5,751,781 * | 5/1998 | Brown et al. | 378/65 |
| 5,807,254 * | 9/1998 | Meulenbrugge et al. | 600/411 |

OTHER PUBLICATIONS

Article by Magin et al., entitled "Miniature Magnetic Resonance Machines", published in *IEEE Spectrum* on Oct. 1997, pp. 51–61.

* cited by examiner

Primary Examiner—Ruth S. Smith
(74) Attorney, Agent, or Firm—Allan M. Lowe; Bella Fishman

(57) ABSTRACT

A radiotherapy machine beam treats a region of a subject while the region and volumes abutting the region are imaged by a magnetic resonance imaging system. The beam and an excitation coil assembly of the imaging system are arranged so the beam is not incident on the coil assembly and magnetic fields derived from the coil assembly do not interact with the beam. The excitation coil assembly includes two spaced winding segments for producing a main DC magnetic field; the segments are located on opposite sides of the region. In one embodiment, wherein the excitation coil assembly is mounted independently of movement of an axis of the beam, the winding segments have a common axis generally aligned with an axis about which the beam axis turns. A treatment couch for the subject fits within aligned central openings of the winding segments. The coil produces main magnetic field lines that extend generally in the same direction as the axis about which the beam turns. In other embodiments, the coil assembly moves with the beam axis and the treatment couch is between the coil segments. In one such embodiment, each winding segment includes a central opening (1) through which the beam axis extends; and (2) generally aligned with magnetic field lines established by and extending between the segments. In another such embodiment, the beam axis extends through a space between the segments, being generally orthogonal to magnetic field lines established by and extending between the segments.

28 Claims, 7 Drawing Sheets

RADIOTHERAPY MACHINE INCLUDING MAGNETIC RESONANCE IMAGING SYSTEM

FIELD OF INVENTION

The present invention relates generally to methods of and devices for treating a region of a subject with a radiotherapy beam and more particularly to such a method and device wherein the region is irradiated by the beam substantially simultaneously with a magnetic resonance imaging system imaging the region.

BACKGROUND OF THE INVENTION

Radiotherapy machines, such as the CLINAC machines manufactured by the assignee of the present invention, generally include a linear electron beam accelerator mounted on a gantry which rotates on an approximately horizontal axis. The electron beam accelerator is usually mounted on the gantry in such a manner that it is offset from the horizontal rotational axis of the gantry. The high energy electron beam emerging from the accelerator is further processed by techniques well-known to those experienced in the art to produce either an electron beam or an X-ray beam suitable for patient treatment. In either case the radiation is collimated in a treatment beam which is caused to travel in a direction perpendicular to the rotational axis of the gantry in such a manner that the axis of the treatment beam intersects the rotational axis of the gantry. The point at which the axis of the treatment beam intersects the rotational axis of the gantry is the focal point of the treatment beam and is referred to as the isocenter of the radiotherapy machine.

In a radiotherapy machine the patient is placed on a treatment couch that can be precisely positioned to locate the treatment region, which is usually a cancerous tumor or lesion in the patient, on the rotational axis of the gantry at the isocenter of the radiotherapy machine. Thus, by rotating the gantry, the source of the treatment beam can be rotated around the patient during treatment, thereby minimizing the amount of treatment radiation passing through any one region of the patient's body near the treatment region while the beam always passes through the treatment region itself. Excessive irradiation of non-diseased tissue, especially those tissues abutting the diseased treatment region, causes undesirable cell damage and cell death in healthy tissue.

Among practitioners of current radiotherapy treatment art it is well-known that minimum abutting cell damage generally occurs when the diseased treatment region in the patient is precisely located at the isocenter of the radiotherapy machine. However, several limitations of the present art make it difficult to achieve the desired precise positioning of the diseased region of the patient at the isocenter of the radiotherapy machine.

One reason for this difficulty is that diseased tissue in a patient usually is surrounded by, or is adjacent to, other soft tissue which is materially similar to the diseased tissue. The similarity of the tissues makes it difficult to precisely define the exact boundaries of the diseased tissue using current diagnostic and imaging techniques appropriate for radiotherapy machines.

One past attempt to overcome this problem has involved using relatively low contrast two-dimensional X-ray-based imaging of the region when the subject is positioned on the radiotherapy machine. The X-ray-based imaging systems have generally relied on detecting X-rays in the same X-ray beam which is used for radiotherapy purposes. However, low contrast two-dimensional X-ray-based imaging of the region does not enable the true position of the region including the tumor or lesion to be definitely located. The difference in X-ray absorbance between different soft tissue structures and between cancerous and non-cancerous soft tissues frequently ranges from small to undetectable. Only the bones, which absorb X-rays more strongly, can be readily imaged and precisely located by this means. Determining the true position of the soft tissue region to be treated is difficult because due to its lack of rigidity the region moves relative to the nearby bones of the subject as a result of unavoidable body movements of the subject on the treatment couch. The uncertainty in determining the true position of the region exists even when fiducial markers are inserted into the tumor because patient movement is likely to cause the fiducial markers to move.

Because the region desired to be treated is usually not located exactly as planned with respect to the isocenter of the radiotherapy system, insufficient quantities of radiotherapy beam energy are deposited in the region desired to be treated and excessive amounts of radiotherapy beam energy are deposited in healthy tissue in a volume abutting the region desired to be treated. Consequently, the tissue in the abutting volume is subjected to undesired and unnecessary damage so healthy organs adjacent the tumor site are damaged.

Because of the general inability to focus the radiotherapy beam with sufficient precision on the region desired to be treated, current medical practice is to increase the irradiated area to include additional tissue volume and to increase the dosage of the radiotherapy beam to ensure complete cell death in the region desired to be treated. The expectation is that all cells in the treated region are killed and possible positioning errors between the beam and the region are compensated. However, such techniques inevitably cause increased collateral radiation damage to the volume abutting the desired region to be treated, in some cases resulting in devastating quality of life effects on the subject. It is, accordingly, an object of the present invention to provide a new and improved method of, and apparatus for enabling a radiotherapy beam to be accurately positioned on a desired region to be treated by the beam.

Another object of the invention is to provide a new and improved method of, and apparatus for enabling a radiotherapy beam to be precisely positioned on a region desired to be treated, wherein the apparatus used to determine whether the beam is properly located is easily retrofitted on existing radiotherapy devices.

An additional object of the invention is to provide a radiotherapy machine including a magnetic resonance imaging system for acquiring 2D and 3D spatially resolved high-contrast images of soft tissue structures and organs within and abutting the region desired to be treated.

An additional object of the invention is to provide a radiotherapy machine including a magnetic resonance imaging system, wherein an excitation coil assembly of the imaging system is arranged so that a radiotherapy beam of the radiotherapy machine is not incident on the coil assembly and wherein the coil assembly is arranged so subjects to be treated can easily be placed in the path of the radiotherapy beam, on a treatment couch.

An additional object of the invention is to provide a new and improved radiotherapy machine in combination with a system for directly detecting the effect of the radiotherapy beam on an irradiated region, particularly the contents of tissue cells in the region, and to spatially resolve the effect of the irradiation to enable real time three-dimensional correlation between the shape, position and intensity of the region actually being irradiated and the known location of a region desired to be irradiated, where a tumor or lesion is located.

A further object of the invention is to provide a new and improved radiotherapy machine in combination with a relatively low cost device for determining whether, and the degree to which tissue in a region desired to be treated by a radiotherapy beam is actually being treated.

Still a further object of the invention is to provide a new and improved X-ray beam therapy device in combination with a magnetic resonance imaging system, wherein secondary electron skin dosage resulting from bombardment of the skin by the X-ray beam is substantially reduced by the magnetic field of the coils of the imaging system.

SUMMARY OF THE INVENTION

In accordance with one aspect of the present invention, these and other objects are achieved by treating a region of a subject with a radiotherapy beam while the region and volumes abutting the region are imaged by a magnetic resonance imaging system. The beam and an excitation coil assembly of the imaging system are arranged so the beam is not incident on the coil assembly and also so that magnetic fields derived from the coil assembly do not perturb the particle trajectories in the beam in the case where the radiotherapy beam is composed of charged particles such as electrons.

The excitation coil assembly of the imaging system preferably includes first and second spaced segments for producing a main DC magnetic field; the segments are located on opposite sides of the region.

In one embodiment, wherein the excitation coil assembly is mounted independently of movement of the treatment beam axis, the first and second excitation coil assembly segments have a common axis substantially coincident with an axis that passes through the region to be treated and about which the beam axis turns. A subject carrying structure, e.g., a treatment couch, fits within aligned central openings of the coil segments. The beam axis passes between the two segments at right angles to the main magnetic field lines produced by and extending between the segments.

In other embodiments, the coil assembly is mounted so it moves as the beam axis moves.

In one of these embodiments, each of the first and second coil segments includes a central opening having a common axis. The beam axis extends through the central openings of both coil segments and is generally aligned with magnetic field lines established by and extending between these segments. In another embodiment, the beam axis extends through a space between the segments and is generally at right angles to magnetic field lines established by and extending between the segments. The latter arrangement, which does not have a central opening in the coil segments, is advantageous because it establishes a higher intensity magnetic field than the arrangements with such an opening.

A feature of the invention is that the magnetic field derived from the excitation coils of the magnetic resonance imaging system is relatively low, sufficient to provide only the minimum necessary spatial resolution and sensitivity for determining whether the radiotherapy beam is incident on the desired region to be treated. The magnetic field density is sufficiently low that conventional copper-wound water cooled coils can be employed to generate the main magnetic field, although superconducting magnetic coil assemblies, cooled to a liquid helium or liquid nitrogen temperature, can be employed if desired.

If a liquid helium-cooled superconducting coil generates the magnetic resonance imaging system main magnetic field, commercially available high temperature superconducting supply leads preferably establish external connections between the superconducting coil and a DC power supply for exciting the superconducting coil. The high temperature superconducting supply leads block heat leakage from the liquid nitrogen temperature at which they are maintained, i.e., 77° K, to the low temperature superconducting coil at 4.2° K. Thereby, the low temperature superconducting coil is not required for reasons of heat leakage to operate in the persistent mode without supply leads connected, hence the current in the coil can be pulsed on and off by an external supply without an unacceptable increase in liquid helium consumption. By pulsing the high temperature superconductor supply leads on and off synchronously with pulsing an electron radiotherapy beam off and on, the magnetic resonance imaging system has no adverse deflection effects on electrons in the radiotherapy electron beam.

To reduce the required strength of the magnetic field derived from the resonance imaging system magnetic coils, a radio frequency pickup coil of the resonance imaging system is preferably a superconductor. This enables the main magnetic coil of the resonance imaging system to have a relatively small size, to facilitate retrofitting the main coil to existing radiotherapy machines and reduce the cost of a facility including the structure of the invention. The superconducting radio frequency coil is preferably a high temperature superconductor formed from oriented high temperature superconducting films grown on metal foils or on planar oxide single crystal substrates. A further feature of the invention is that leakage magnetic fields originating in the radiotherapy machine are decoupled from magnetic fields originating in the magnetic resonance imaging system and leakage magnetic fields originating in the magnetic resonance imaging system are decoupled from the radiotherapy linear accelerator. The decoupling is preferably provided by compensating coils positioned outside the imaging system coils and by a coil or coils surrounding the linear accelerator and its associated components.

A feature of the present invention is the capability of the magnetic resonance imaging system to detect changes in nuclear magnetic resonance spectral parameters of the image region due to the effects of the radiotherapy beam irradiating the tissue desired to be treated by the beam.

At thermal equilibrium in a magnetic field, the magnetic moment of a nucleus is aligned with the magnetic field. When perturbed from this alignment, the magnetic moment precesses around the applied field at the characteristic resonance frequency of the particular nuclear species (often a hydrogen nucleus or proton). The variation of the applied magnetic field at different atomic sites in a molecule due to the shielding effects of the surrounding electrons causes small shifts in the resonance frequencies of similar nuclei. The nature of the environment of the resonating nuclei determines the rate at which the resonance decays, or relaxes. These differences in resonance frequencies can be resolved and used to analyze molecular structures. Alternatively, the resonance frequencies can be modified by the imposition of a magnetic field gradient across a sample in which case the resonance frequency is a function of the position of a particular nuclear spin within the sample. This forms the basis of nuclear magnetic resonance imaging systems.

In either case, application of an rf pulse with a frequency close to that of the natural resonance frequency of the spins is used to perturb the nuclear magnetic moment. The perturbation rotates the nuclear magnetic moment away from its alignment with the applied magnetic field. A rotation of 90° produces a maximum magnetization transverse to the magnetic field while a 180° rotation results in an inversion of the initial magnetization but no transverse magnetization. It is the transverse component of magnetization which precesses about the applied magnetic field and which can be detected in an NMR spectrometer. Following a perturbation, two relaxation times characterize the return to thermal equilibrium. In addition to precessing, the transverse magnetization decreases in amplitude with a characteristic time constant T2, the spin-spin relaxation time. The component of magnetization parallel to the applied field returns to its initial value with a characteristic time constant T1, the spin-lattice relaxation time. Both of these relaxation times are affected by the magnetic influences of neighboring atoms and molecules. In particular, the presence of free radicals with their strong electronic magnetic moment can modify the relaxation times and resonance frequencies of nearby nuclei. The measurement of resonance frequencies and relaxation times can be combined with NMR imaging methods to provide NMR spectral data which is correlated with spatial position.

Because of the high sensitivity of the NMR spectral parameters to differences in the magnetic environment of nuclei in different types of soft tissue i.e. between the tissues in different body organs or between cancerous and non-cancerous tissues, the NMR image of soft tissue structures achieves much greater contrast than an X-ray image of the same tissue volume. Additionally the MR image contains 3D rather than 2D positional information. The position of the cancerous tumor or lesion in the soft tissue can therefore be determined directly on the radiotherapy machine with much greater precision than by inferring the presumed position of the tumor with reference to the position of the nearby bones obtained from an X-ray image.

In addition, because of the large change in NMR spectral parameters induced by the presence of free radicals, which are one of the primary products of the irradiation of tissues by the radiotherapy beam, both the spatial location and the intensity of the irradiation effects of the radiation therapy beam on the tissues within the imaged volume can be determined in real time during treatment.

In accordance with an aspect of the present invention, the analytical capability of a magnetic resonance imaging system is used to detect changes in nuclear magnetic resonance spectral parameters due to effects of the radiotherapy beam irradiating the tissue. The radiotherapy beam incident on selected tissue causes free radicals and ionization products to be produced in the tissue. The presence of these can be detected and imaged. The radiotherapy beam, the high intensity magnetic fields and the rf pulse of the magnetic resonance imaging system thus interact to enable three-dimensional spatial distribution information to be derived for the radiation dose of the radiotherapy beam deposited in the treated and abutting tissue during the treatment process. The three-dimensional information is derived by using known magnetic resonance imaging techniques and by correlating the detected data with the beam axis position and the known beam cross-sectional geometry and intensity. The three-dimensional information relating to the spatial distribution of the radiotherapy beam on the treated tissue is correlated with previously gathered and therefore known three-dimensional data concerning the position of the cancerous tissue desired to be treated. Thereby, the radiotherapy beam can be confined to the tissue desired to be treated and controlled so it is not incident on the abutting tissue. This enables the total radiation dose to the subject from the beam to be reduced and collateral damage to healthy tissue minimized. An MR image in absence of radiation will show cancerous tissue. With the beam on, the MR image will show the extent of tissue being irradiated.

The above and still further objects, features and advantages of the present invention will become apparent upon consideration of the following detailed description of specific embodiments thereof, especially when taken in conjunction with the accompanying drawings.

DESCRIPTION OF THE PREFERRED EMBODIMENT

Figure 1:
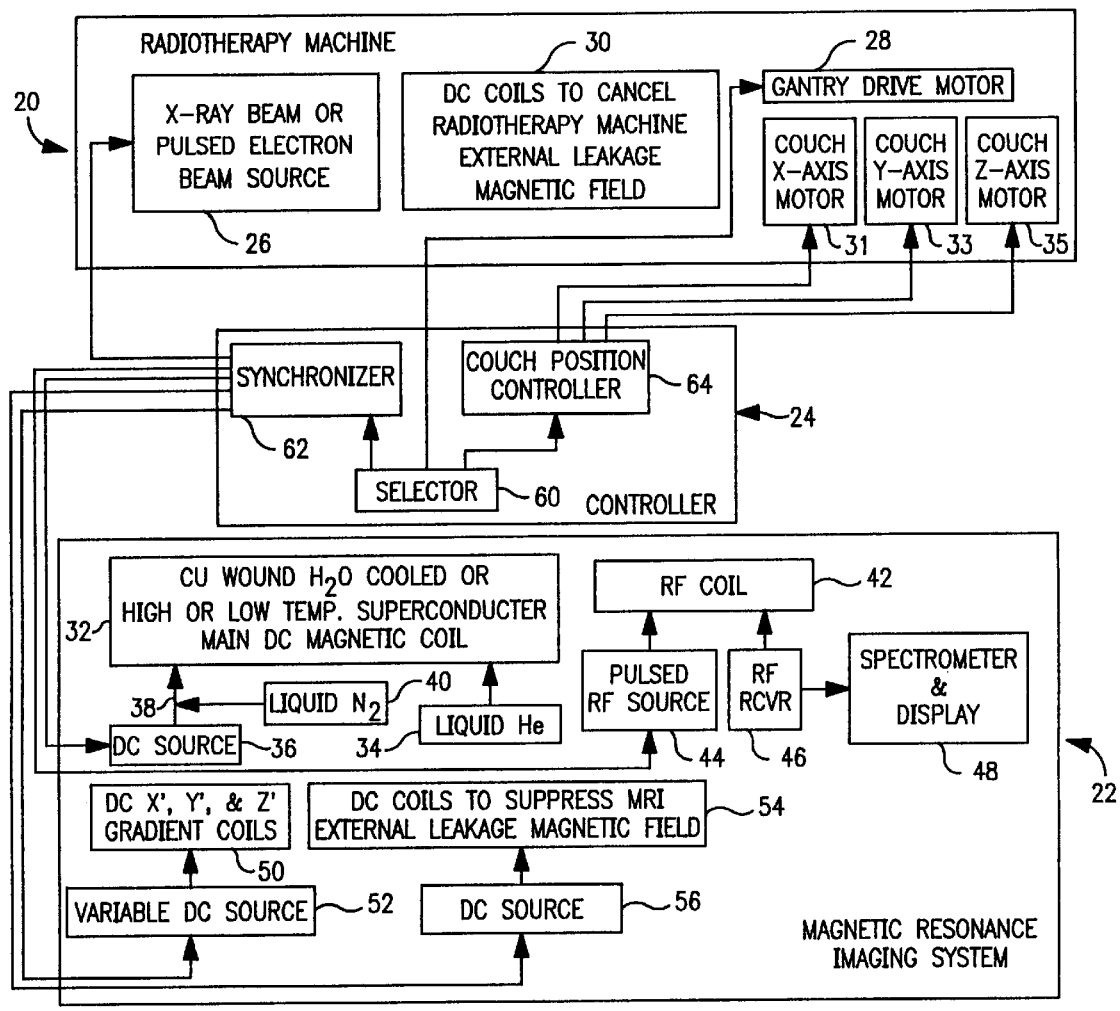
FIG. 1 is a block diagram of the present invention with several preferred embodiments outlined.

Reference is now made to the block diagram of FIG. 1, wherein the apparatus of the present invention is illustrated as including a relatively conventional radiotherapy machine 20, a magnetic resonance imaging system 22 and controller 24 for devices included in machine 20 and system 22. Radiotherapy machine 20 includes a radiotherapy beam source, in the form of an X-ray beam or pulsed electron beam source 26, a gantry for carrying source 26, drive motor 28 for the gantry, and a treatment couch on which a subject (patient) is located. The treatment couch includes a subject receiving bed that is selectively positioned in the horizontal plane along X and Z axis directions and in the vertical, Y axis direction; horizontal and vertical movements of the bed are provided by horizontal and vertical drive motors 31, 33 and 35. Radiotherapy machine 20 also includes coil 30 which encircles the linear accelerator and substantially cancels external leakage magnetic fields associated with the linear accelerator so these leakage fields do not have an effect on the operation of magnetic resonance imaging system 22.

Magnetic resonance imaging system 22 includes a main DC magnetic coil assembly 32 having two spaced winding segments between which is located a region to be treated by the radiotherapy beam. The winding segments of assembly 32 are supplied with DC current by source 36 to produce the main magnetic DC field of system 22. Magnetic coil assembly 32 is positioned to produce a main DC magnetic field in the region of the subject at the location of the tissues desired to be destroyed by the radiotherapy beam of machine 20. The magnitude of the DC magnetic field produced by assembly 32 is sufficient to precess protons of body tissue cells of the subject in the region. Assembly 32 can include copper wire wound water cooled winding segments (to minimize the cost of system 22) or high temperature superconducting winding segments cooled by a liquid nitrogen source or low temperature wire winding segments cooled to liquid helium temperatures by liquid helium source 34.

If the coils of assembly 32 are low temperature superconducting coils, they are preferably formed of niobium titanium (NbTi) or niobium tin ($Nb_3Sn$) wire. Such superconducting coils provide a higher magnetic field than is provided by conventional copper water cooled windings, given the constraints set by power consumption, cooling water supply and space available to accommodate the conventional copper windings.

If the low temperature superconducting coils are employed in assembly 32 to generate the main magnetic field of imaging system 22, the coils of assembly 32 are preferably connected to source 36 by high temperature superconducting leads 38, formed of commercially available materials. Leads 38, being maintained at a superconducting temperature of 77° K by liquid nitrogen source 40, block heat leakage from source 36 to the 4.2° K superconducting coils of assembly 32 so the coils of assembly 32 are not required to operate in a persistent mode. Since the coils of assembly 32 need not be operated in the persistent mode, the coils can be pulsed on and off, as is necessary if the beam of radiotherapy machine 20 is an electron beam. If the radiotherapy beam of machine 20 is an electron beam, the electron beam must be pulsed and the magnetic fields of imaging system 22 must be pulsed off when the electron beam is produced, so the imaging system magnetic fields do not deflect the electron beam charge carriers.

Magnetic resonance imaging system 22 also includes rf coil 42 which excites protons in the imaged region treated by the radiotherapy beam so the protons precess at a frequency determined by (1) the atoms containing the protons; and (2) the magnitude of the magnetic fields where the protons are located. Rf coil 42 is either a conventional wire wound coil or is a high temperature superconductor, cooled to liquid nitrogen temperatures or a low temperature superconductor, cooled to a temperature close to that of liquid helium.

Rf coil 42 is supplied with rf energy by pulsed rf source 44 which derives short duration pulses having a carrier frequency related to the precessing frequency of protons in the imaged and treated region. Rf receiver 46 responds to rf energy from the precessed protons and coupled back to coil 42 after the pulse from source 44 has subsided. The frequency of the energy coupled by coil 32 to receiver 46 is determined by the precessing frequency of protons in the region of the subject exposed to the DC magnetic fields of system 22, and the types of atoms in the region of the subject coupled to the magnetic fields derived from imaging system 22. By employing rf excitation pulses from rf source 44 to align the spins and then using delayed probe pulses to monitor the time-dependent signal amplitude at the various precession frequencies, it is possible to derive the relaxation times T1 and T2. Appropriate pulse sequences to accomplish this have been developed by those skilled in the art of magnetic resonance imaging. For example an 180° excitation pulse to align the spins followed by a 90° probe pulse may be employed to measure T1 and a 90° excitation pulse to align the spins followed by a 180° probe pulse may be used to monitor T2. More complex pulse sequences well known to those skilled in the art are employed to improve sensitivity and accuracy and these are combined with established signal processing techniques to provide a spatially resolved image where the pixels are weighted according to the local values of the relaxation times. Since the precessing frequency of protons in the imaged and treated region and in particular the values of the relaxation time parameters T1 and T2 are affected by the irradiation products of the radiotherapy beam, the frequency and the time-dependent amplitude of the rf energy coupled back to coil 42 is a function of whether or not the radiotherapy beam is incident on the imaged tissue.

The rf receiver 46 supplies an rf signal to spectrometer of unit 48 and display unit 48. The spectrometer preferably combines the capability of fast Fourier transform analysis of chemical shift spectra employed in chemical nuclear magnetic resonance systems with the T1 and T2 relaxation time measurement capability and gradient coil driving electronics of magnetic resonance imaging systems, while the display is of the three-dimensional type usually used in magnetic resonance imaging systems. Thereby, spectrometer and display unit 48 includes a fast Fourier transform computer program to determine the frequency content of the rf energy coupled by coil 42 to receiver 46.

Because spectrometer and display unit 48 includes a fast Fourier transform program and relaxation time measurement capability, magnetic resonance imaging system 22 uses the analytical capability of system 22 to detect changes in the nuclear magnetic resonance (NMR) spectral parameters (including the relaxation times) derived from the region irradiated by the radiotherapy beam of machine 20. Characteristic changes in the local NMR spectral parameters result from the effects of irradiation by the radiotherapy beam on tissue in the region. Consequently, spectrometer and display unit 48 is able to provide three-dimensional information concerning the spatial distribution of the radiotherapy beam from machine 20 on tissue in the subject while the tissue is being treated by the radiotherapy beam. The three-dimensional information is derived from the display of unit 48 and is correlated either by an operator or automatically by a computer (not shown) with information concerning the location of the desired area to be treated, e.g., the position of the cancerous cells in the patient. In response to this correlation, the position of the patient and therefore of the tissue irradiated by the radiotherapy beam is moved by the operator controlling motors 31, 33 and 35 for the position of the treatment couch of machine 20 or by an automatic feedback system (not shown) for controlling couch position.

Basically, spectrometer and display unit 48 monitor changes in the nuclear magnetic resonance spectral parameters of the magnetic resonance imaging system 22. These changes in the nuclear magnetic resonance spectral parameters are directly responsive to the effects of irradiation of the cancerous cells being treated by the radiotherapy beam. This information enables real time three-dimensional correlation between the shape, position and intensity of the irradiated volume and the location of the region desired to be treated, i.e., the region containing the cancerous cells.

If rf coil 42 includes a superconductor, preferably a high temperature superconductor, cooled to the 77° K temperature of liquid nitrogen, the magnitude of the main magnetic field derived from the coil of assembly 32 can be substantially reduced. This enables the magnetic coil of assembly 32 to be substantially reduced in volume to facilitate retrofitting the winding segments of this coil assembly to radiotherapy machine 20. Preferably, the high temperature superconductor included in coil 42 is made from oriented high temperature superconductor films grown on metal coils with appropriate buffer layers or on planar oxide single crystal substrates.

Magnetic resonance imaging system 22 also includes assembly 50 containing DC gradient coils for X', Y' and Z' coordinate axes that are somewhat different from the X', Y' and Z' coordinate axes for the couch of machine 20. The X' and Z' axes are in the horizontal plane but are displaced 45° from the X and Z axes while the vertical Y and Y' axes are coincident. The gradient coils of assembly 50 are supplied with variable amplitude DC currents from source 52 such that at different times the amplitudes of the gradient magnetic fields produced by the coils of assembly 50 vary.

The gradient coils of assembly 50 are mounted so the radiotherapy beam is not incident on them and the gradient coils do not interfere with the beam supplied by radiotherapy machine 20 to the subject. To this end, the X' and Z' coils, which are at right angles to the axis of the radiotherapy beam incident on the subject, are mounted on the coils of assembly 32, as described in detail infra. The coils of assembly 50 which establish the Y' axis magnetic field that is either vertical or which extends in the same general direction as the axis of the radiotherapy beam incident on the subject are positioned in different vertical planes or in different planes at right angles to the beam axis and include openings enabling the beam to propagate through them.

If machine 20 irradiates the subject with an electron radiotherapy beam, source 52 is pulsed on and off simultaneously with source 36 pulsing the coils of assembly 32 on and off so the magnetic fields derived from the gradient coils are not produced while the electron beam is on. Thereby, the gradient magnetic fields produced by the gradient coils of assembly 50 do not have a tendency to deflect the pulsed electron radiotherapy beam.

If machine 20 irradiates the subject with an X-ray radiotherapy beam, magnetic resonance imaging system 22 also includes DC coils of assembly 54; the coils of assembly 54 are supplied with DC current by source 56. The coils of assembly 54 are arranged, as described infra, to produce magnetic fields to suppress leakage magnetic fields derived from the coils of assemblies 32 and 50 of imaging system 22 so these leakage fields are not coupled to the linear accelerator structure of radiotherapy machine 20. If radiotherapy machine 20 is used exclusively to derive an electron beam, the coils of assembly 54 and DC source 56 are not necessary because the magnetic fields from assemblies 32 and 50 are not on while the linear accelerator of the radiotherapy machine is producing a pulsed electron radiotherapy beam.

Controller 24, which can be operated by an operator or automatically in a fully automatic system, includes selector 60, synchronizer 62 and couch position controller 64. Selector 60 supplies signals to couch position controller 64 to activate X, Y and Z axis drive motors 31, 33 and 35 for the patient receiving bed movably mounted on the couch of radiotherapy machine 20 so these drive motors are energized at times while (1) no beam from radiotherapy machine 20 is incident on the subject on the couch; and (2) the coils of assemblies 32 and 50 and the rf coil 42 of imaging system 22 are deactivated. At other times, selector 60 controls synchronizer 62 so radiotherapy beam source 26, if it is an electron beam source, is pulsed on while DC sources 36 and 52 are pulsed off and vice versa. Similarly, pulsed rf source 44 is controlled by synchronizer 62 to be inactive while an electron beam is derived from source 26.

Figures 2, 3:
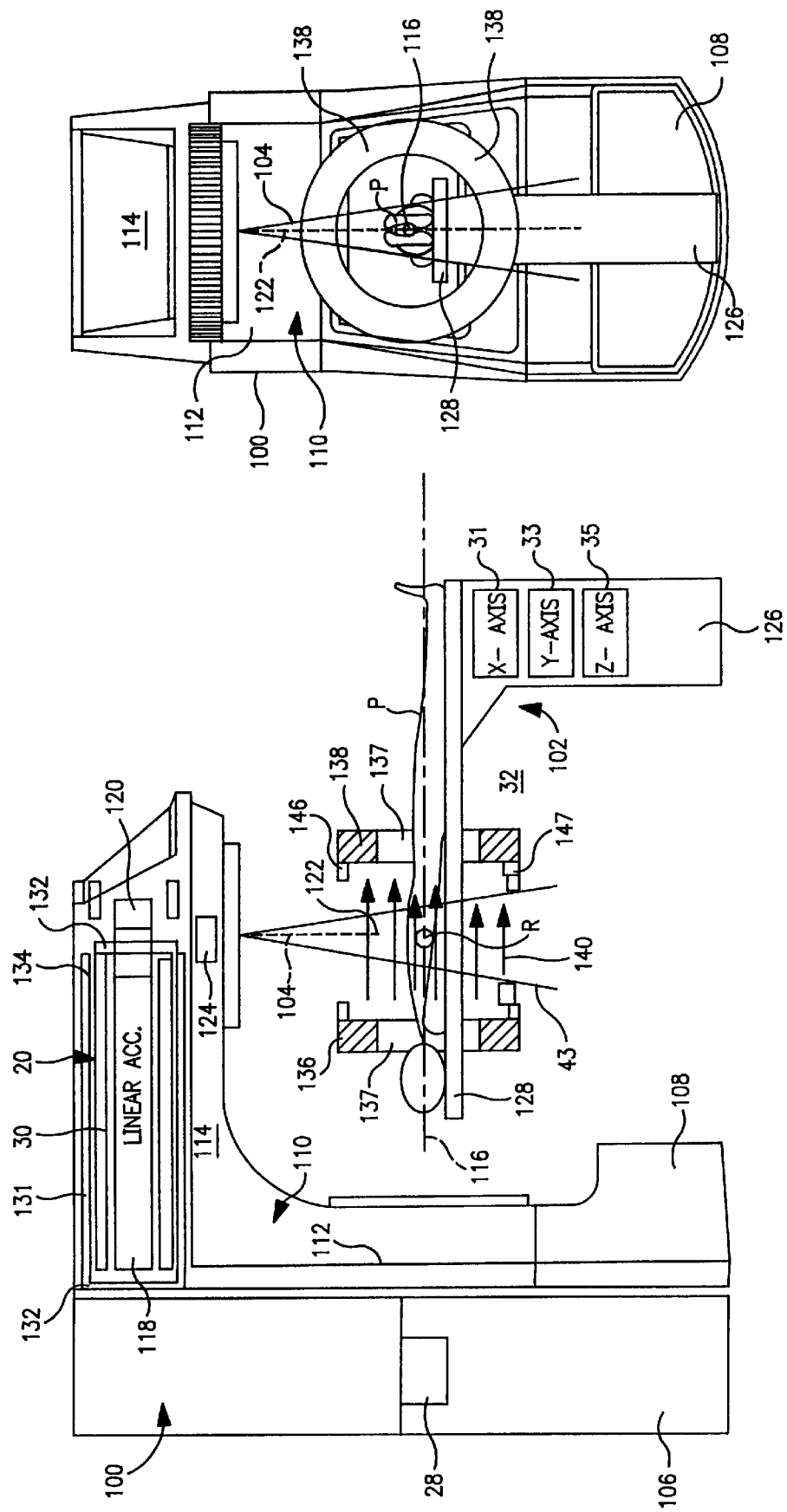
FIG. 2 is a side view of a radiotherapy machine, in combination with spaced stationary DC excitation coil segments of a magnetic resonance imaging system, wherein (1) a radiotherapy beam axis is generally at right angles to the direction of main magnetic flux lines extending between the spaced segments, (2) a treated region of a subject is in a space between the segments, and (3) the segments include a central opening to accommodate the subject.
FIG. 3 is a front view of the apparatus illustrated in FIG. 2.

Reference is now made to FIGS. 2 and 3 of the drawing wherein radiotherapy machine 20 is illustrated as including housing 100 (that carries radiotherapy beam source 26) and treatment couch 102 on which patient P is located. Patient P includes cancerous tissue region R that is irradiated by radiotherapy beam 104, derived from the radiotherapy beam source of machine 20. Housing 100 includes floor mounted upright compartment 106, floor-mounted pedestal 108 and gantry 110 comprised of vertically extending shoulder 112 to which horizontally extending arm 114 is fixedly mounted. Gantry 110 is rotated about horizontal axis 116 by gantry drive motor 28, fixedly mounted in upright compartment 106. Gantry arm 114 carries linear accelerator 118 and associated electron optics including bending magnet 120 which bends a highly energetic electron beam produced by the linear accelerator. The electron beam propagates in accelerator 118 in the horizontal direction, parallel to axis 116 and is deflected by the electron optics of accelerator 118 along beam axis 122 that is at right angles to axis 116. In some radiotherapy machines, radiotherapy beam 104 is an electron beam while in other radiotherapy machines, the radiotherapy beam is comprised of X-ray photons. In the latter case, X-ray target 124 is positioned in the path of the electron beam derived from the linear accelerator and the electron optics including bending magnet 120.

The electron optics for the beam derived by linear accelerator 118 and X-ray optics for the beam derived from X-ray target 124 are such that radiotherapy beam 104 is focused on region R of patient P at the isocenter of the radiotherapy machine where the cancerous tissue to be treated is located. Region R, the region desired to be treated by radiotherapy beam 104, is at the intersection of axes 116 and 122.

To assist in positioning region R at the intersection of axes 116 and 122, treatment couch 102 includes fixed floor-mounted platform 126 which carries X axis, Y axis and Z axis motors 31, 33 and 35 for moving patient-carrying bed 128 in three mutually orthogonal directions, such that bed 128 is moved in the horizontal plane in the X and Z axes directions and is moved in the vertical direction along the Y coordinate axis.

Radiotherapy machine 20, as previously described, is conventional. In the present invention, wherein magnetic resonance imaging system 22 is included in combination with machine 20, leakage magnetic fields produced by linear accelerator 118 and bending magnet 120 are preferably decoupled from magnetic fields of the magnetic resonance imaging system. To this end, leakage field cancellation DC coils 30 surround linear accelerator 118. Preferably DC coils 30 comprise cancellation coil 130, approximately solenoidal in form, that surrounds accelerator 118 and cancellation coil 133 that surrounds bending magnet 120. Solenoid coil 130 in turn surrounds an iron sleeve 131 including oppositely disposed end caps 132 between which extends iron tube 134. This provides a magnetic return path for the majority of the leakage field from the focusing solenoid of accelerator 118 and reduces the current required in cancellation coil 130. One of end caps 132 has a central opening through which extend electric leads for supplying power to linear accelerator 118. Tube 134 has an opening aligned with axis 122; the opening in tube 134 has a diameter sufficient to enable the electron beam derived by accelerator 118 to pass in an unhindered manner out of the leakage field cancellation system for the accelerator. Additional openings are provided in endcaps 132 and tube 134 for waveguides, electrical supply leads and coolant.

In the embodiment of FIGS. 2 and 3, main DC excitation coil assembly 32, rf coil 42, gradient coils 50 and leakage field suppression coils 54 are fixedly mounted by struts (not shown) on pedestal 108 or the floor carrying the pedestal so movement of these coils is independent of turning of linear accelerator 118 about axis 116. Main DC excitation coil 32 preferably carries rf coil 42, gradient coils 50 and leakage field suppression coils 54.

Main excitation coil 32 includes two vertically extending, horizontally spaced winding segments 136 and 138, each having a central opening 137 generally aligned with axis 116. Coil segments 136 and 138 surround patient P and bed 128. Coil segments 136 and 138 produce horizontally extending main DC magnetic field lines 140 that are directed generally at right angles to radiotherapy beam axis 122 and extend through treatment region R of patient P. Coil segments 136 and 138 are spaced from each other so region R is between them. Beam 104 extends between coil segments 136 and 138 so the radiotherapy beam does not intersect any portion of coils 32, rf coil 42, gradient coils 50 or leakage field suppression coils 54.

Figure 8:
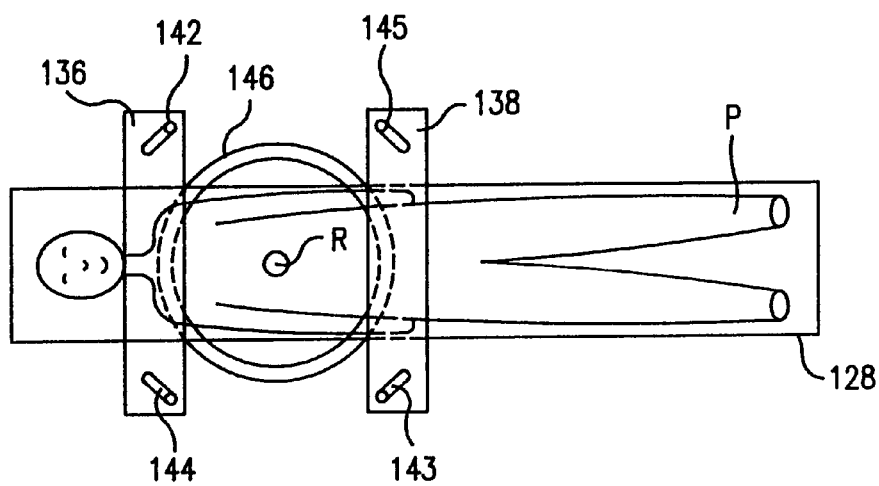
FIG. 8 is a top view of a portion of the apparatus illustrated in FIG. 6, particularly of the position of X, Y, and Z axis gradient coils of the magnetic resonance imaging system.

To these ends, as illustrated in FIG. 8, X axis gradient DC coils 142, 143 are positioned at and carried by a pair of diagonally opposite corners of DC excitation coil segments 136 and 138. Z' axis gradient DC coils 144, 145 are positioned at and carried by the remaining pair of diagonally opposite corners of segments 136 and 138. Coils 142–145 are mounted on the center portions of coil segments 136 and 138, at the level of bed 128 to produce in region R horizontally directed DC gradient field lines that are at right angles to each other. Y' axis gradient DC coils 146, 147 are positioned at upper and lower edges of coil segments 136 and 138 to produce vertically directed magnetic field lines through region R. Rf coil 42 is fixedly mounted inside of, and to coils 142–145 to supply an rf field to region R and respond to an rf field coupled back to it from region R after the applied rf field has subsided.

Figure 10:
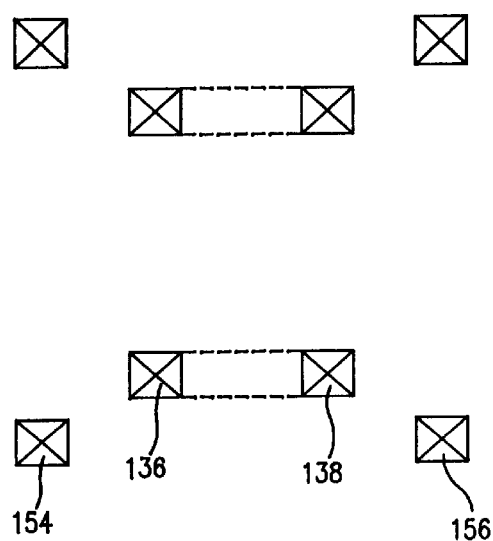
FIG. 10 is a side view of the magnetic resonance imaging coil of FIG. 6, in combination with a coil arrangement for substantially canceling leakage magnetic fields from the coil.

To suppress the leakage field produced by coil segments 136 and 138, and thereby confine magnetic field lines 140 to the region between the coil segments so the leakage field does not have an effect on the magnetic field linear accelerator 118, DC field suppression coils 54 are formed as a pair of segmented coil windings 154 and 156, as illustrated in FIG. 10. Segments 154 and 156 are respectively carried by and located outside of coil segments 136 and 138 and have central openings with internal diameters slightly less than the internal diameters of coil segments 136 and 138. Coil segments 152 and 154 have external diameters slightly in excess of the external diameters of coil segments 136 and 138. Coil segments 152 and 154 produce magnetic fields which are directed oppositely to and have a magnitude substantially equal to the leakage fields of winding segments 136 and 138 to provide the desired cancellation; this result is achieved by appropriate DC excitation and winding arrangements of coil segments 152 and 154.

Figure 5:
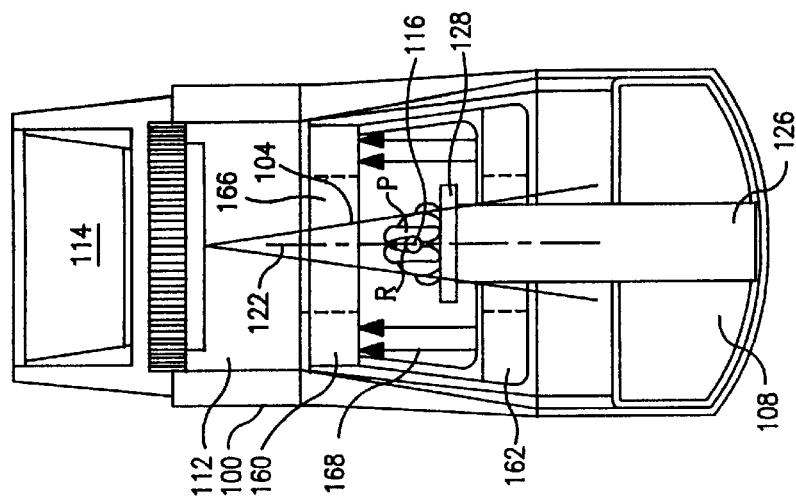
FIG. 5 is a front view of the apparatus illustrated in FIG. 4.
Figure 4:
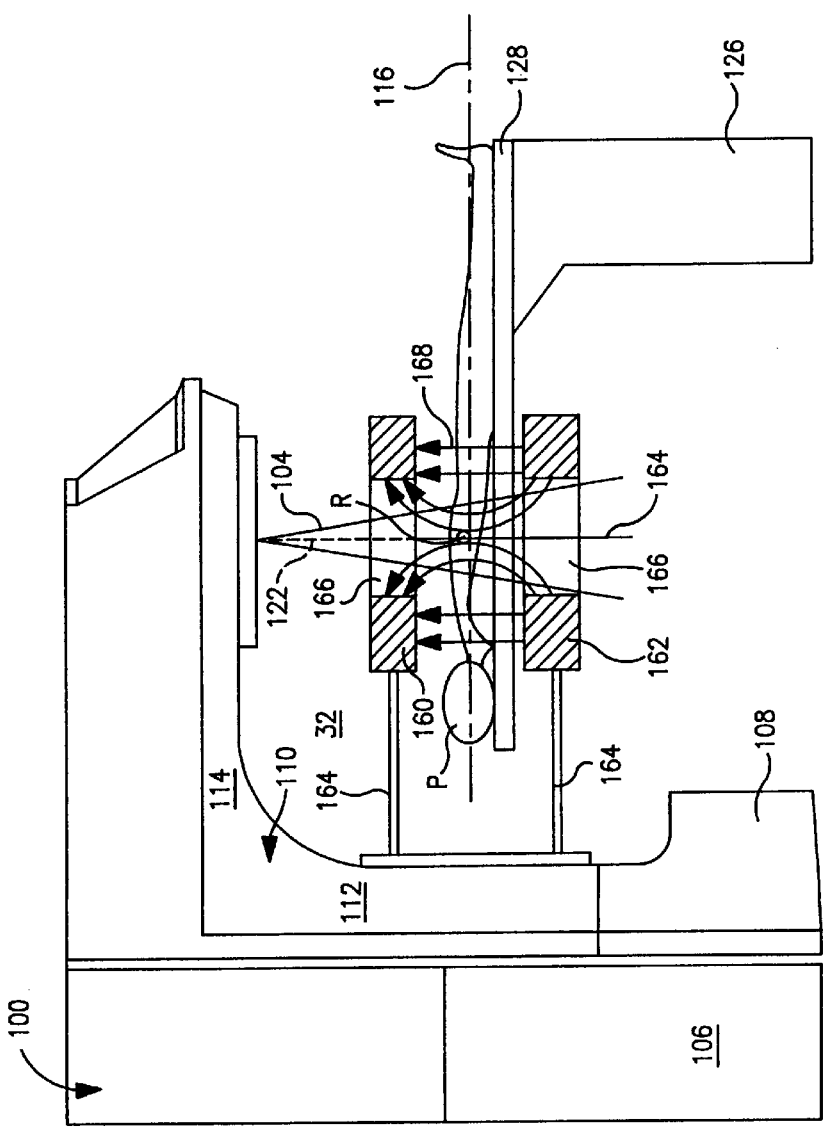
FIG. 4 is a side view of a radiotherapy machine, in combination with spaced DC excitation coil segments of a magnetic resonance imaging system, wherein (1) the segments are mounted so an axis of a radiotherapy beam goes through a central opening of the segments, in general alignment, with main magnetic field lines extending between the segments, (2) a treated region of the subject is in a space between the segments, and (3) the segments include a central opening to accommodate the beam.

Reference is now made to FIGS. 4 and 5 of the drawing, wherein main DC excitation coil assembly 32, rf coil 42, gradient coils 50 and leakage suppression coils 54 are configured substantially the same as illustrated in FIGS. 2, 3. However, in the embodiment of FIGS. 4 and 5, coil assembly 32, rf coil 42, gradient coils 50, and leakage suppression coils 54 are carried by and fixedly attached to gantry 110 so all of these coils rotate about axis 116. To simplify the drawing, in FIGS. 4 and 5 only split winding segments 160 and 162 of coil assembly 32 are illustrated, it being understood that rf coil 42, gradient coils 50 and leakage suppression coils 54 are configured basically the same in the embodiment of FIGS. 4 and 5 as in the embodiment of FIGS. 2, 3. Winding segments 160 and 162 are fixedly connected to gantry 110 by struts 164 and spaced from each other so patient P and bed 128 are between them.

Each of coil segments 160 and 162 includes a central opening 166 having a common axis 164 that is substantially coincident with axis 122 of radiotherapy beam 104 and extends through region R. Winding segments 160 and 162 are wound and energized so that main DC magnetic field lines 168, which extend between the coil segments, are generally in planes parallel to axes 122 and 164.

Winding segments 160 and 162 of coil assembly 32, as well as rf coil 42, gradient coils 50 and leakage suppression coils 54, are arranged so beam 104 is not incident on any of these coils or winding segments. Because of the substantial coincidence between axis 164 of openings 166 of winding segments 160 and 162 and radiotherapy beam axis 122, the excitation winding segments of the embodiment of FIGS. 4 and 5 have a smaller center opening than the center opening of the winding segments in the embodiments of FIGS. 2, 3. As a result of the smaller center opening in the embodiments of FIGS. 4 and 5, winding segments 160, 162 supply a higher imaging DC magnetic field strength to region R than winding segments 136, 138 for winding segments having the same size and other characteristics. The embodiment of FIGS. 4 and 5 also enables an operator to have better physical access to patient P than is provided with the configuration of FIGS. 2, 3. Further, the embodiment of FIGS. 4 and 5 is less confining to the patient, to reduce psychological stress on the patient.

Figures 6, 7:
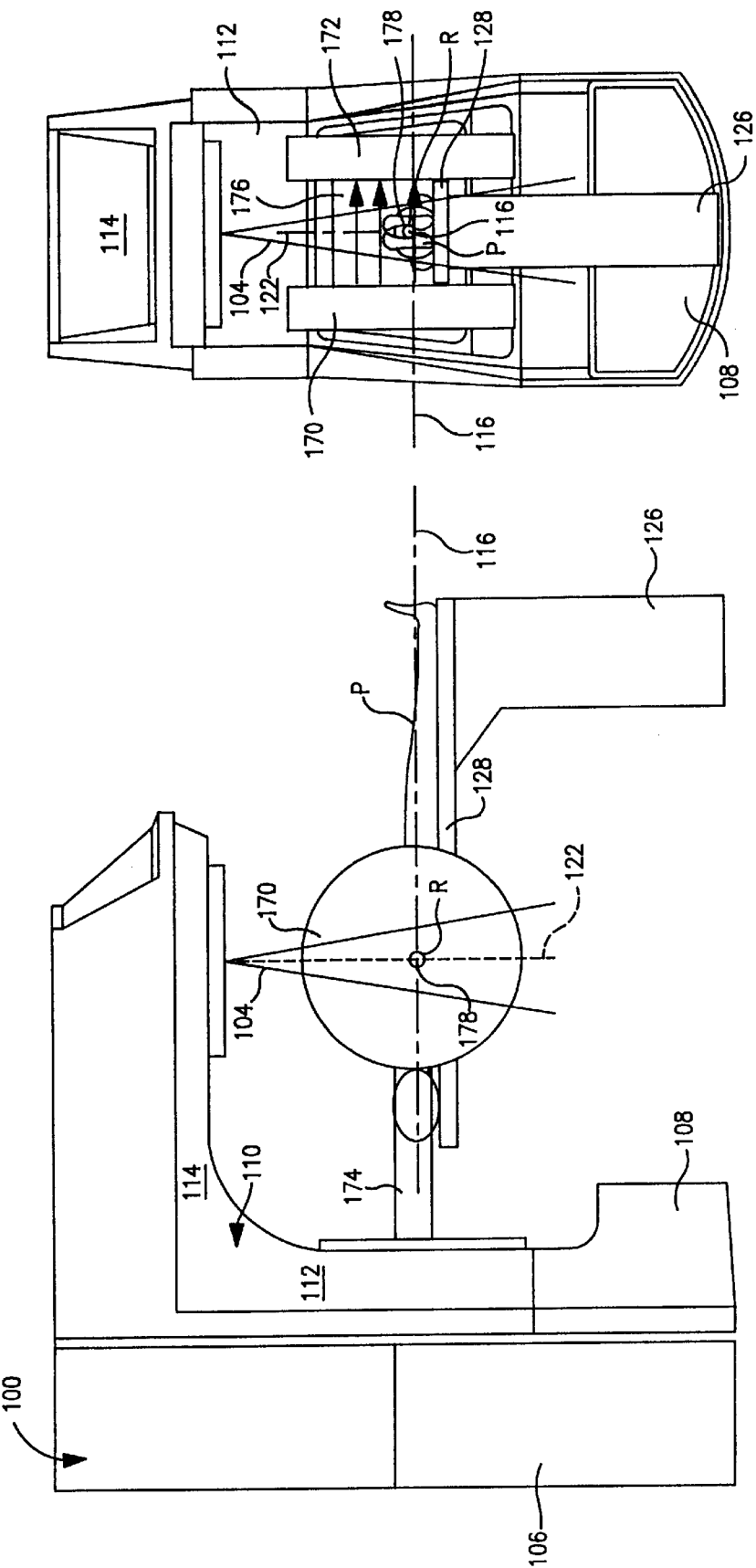
FIG. 6 is a side view of a further embodiment of the present invention, wherein (1) spaced DC excitation coil segments of a magnetic resonance imaging system move with a radiotherapy beam axis and are arranged so main magnetic field fines derived from the coil segments are generally at right angles to the radiotherapy beam axis, (2) the treatment region is between the two coil segments, and (3) the segments do not have a central opening.
FIG. 7 is a front view of the apparatus illustrated in FIG. 6.

In accordance with a further embodiment, illustrated in FIGS. 6 and 7, main DC excitation coil 32 includes spaced pancake-like winding segments 170 and 172. Segments 170 and 172 extend parallel to each other and are spaced from each other by an amount sufficient to enable bed 128 and patient P to fit between them. Winding segments 170 and 172 and compensating coils 154 are arranged so that the common axis 178 of rotational symmetry thereof is orthogonal to both radiotherapy beam axis 122 and gantry axis 116 about which linear accelerator 118 turns. Consequently, beam 104 passes without obstruction between winding segments 170 and 172 to obviate the need for a central opening in the winding segments. (In FIGS. 6 and 7, only winding segments 170 and 172 of coil assembly 32 are illustrated, but rf coil 42, gradient coils 50 and leakage compensation coils 54 are fixedly mounted with coil assembly 32, as described supra in connection with FIGS. 2 and 3.) Winding segments 170 and 172 and the coils carried by them are fixedly mounted to gantry 110 by struts 174.

Coil winding segments 170, 172 produce main DC magnetic field lines 176 that extend at right angles to radiotherapy beam axis 122. Because there is no central opening in winding segments 170, 172, the strength of the main DC magnetic field produced by winding segments 170, 172 is greater than the main DC magnetic field strengths produced by winding segments 136, 138 or 160, 162 in the embodiments of FIGS. 2 and 3 or FIGS. 4 and 5, for the same characteristics of all three sets of winding segments.

All of winding segments 170, 172, rf coil 42, gradient coils 50 and leakage field suppression coils 54 are arranged in each of the embodiments of FIGS. 2 and 3, 4 and 5 and FIGS. 6 and 7 such that radiotherapy beam 104 is not incident on any portions thereof. If the radiotherapy beam were incident on any portions of the coils, secondary X-rays would be produced with detrimental effects on patient P. In addition, there would be an inefficient waste of the radiotherapy beam energy on the incident coil parts.

In the embodiments of FIGS. 4 and 5 and 6 and 7, wherein the coils are mounted on gantry 110 so the coils rotate with the gantry about axis 116, the angular position of coils 32 can be determined at all times. This result is achieved by monitoring the angular position of gantry 110 by mounting a conventional angular position detector (not shown) on the gantry about axis 116. The angular position detector for gantry 100 supplies a signal indicative of gantry angular position to spectrometer and display unit 48. Unit 48 responds to the signal indicative of gantry, angular position to compensate for variations in the magnetic field established by coil 32 as the coil is turned to different angular positions about axis 116.

Figure 9:
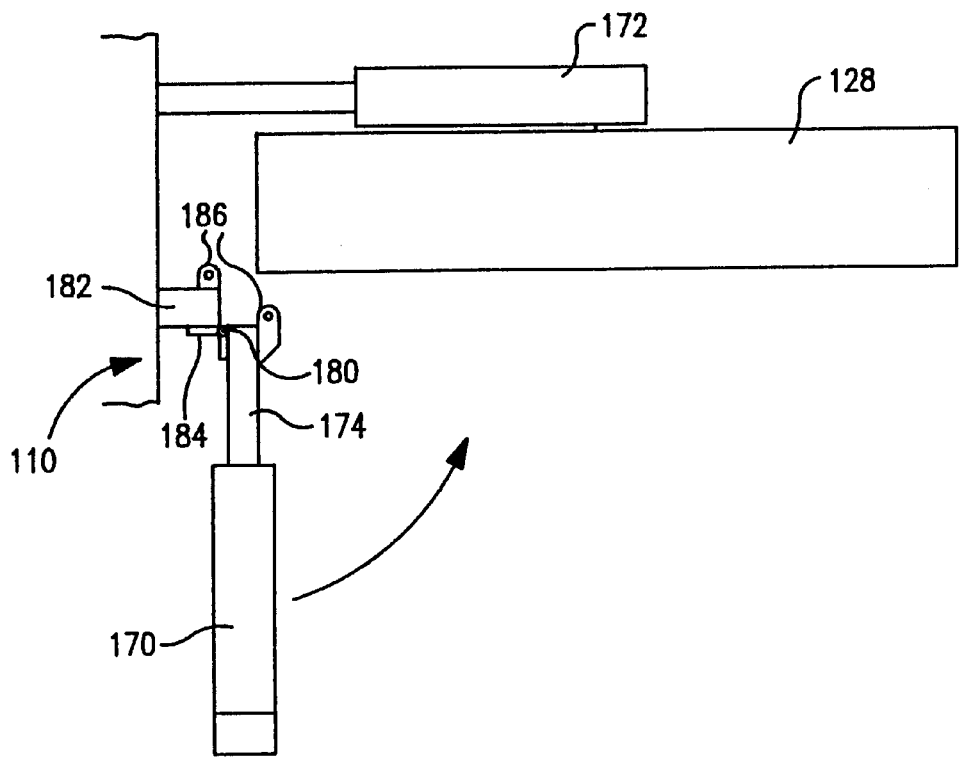
FIG. 9 is a top view of the apparatus illustrated in FIG. 6, wherein a coil segment of the magnetic resonance imaging system is turned 90° to enable ease of access by a patient to the treatment couch of the radiotherapy device.

One possible problem with the embodiment of FIGS. 6 and 7 is that it is difficult for patient P to get on and off bed 128 between spaced winding segments 170 and 172. To solve this problem, winding segments 170 and 172 are physically mounted as illustrated in the top view of FIG. 9, wherein the strut 174 which carries winding segment 170 is mounted so the strut and winding segment can selectively pivot about vertical axis 180. To this end, gantry 110 includes shoulder 182 on which one leaf of hinge 184 is fixedly mounted. The other leaf of hinge 184 is fixedly mounted to strut 174 that carries winding segment 170. In normal operation, when current is applied to winding segments 170, 172, hinge 184 is maintained in place by locking mechanism 186. Prior to patient P beginning treatment by beam 104 or when treatment has been completed, locking mechanism 186 is released and winding segment 170 is swung open so patient P can move on to and off of bed 124.

Winding segment 172, maintained in a fixed position at all times on gantry 110, carries both of the Y' axis gradient coils 186, 187 of assembly 50 and X' and Z' axes gradient coils of assembly 50; the other two X' and Z' axis gradient coils 183 and 185 are carried by winding segment 170, in a manner described supra in connection with FIG. 8.

Figure 11:
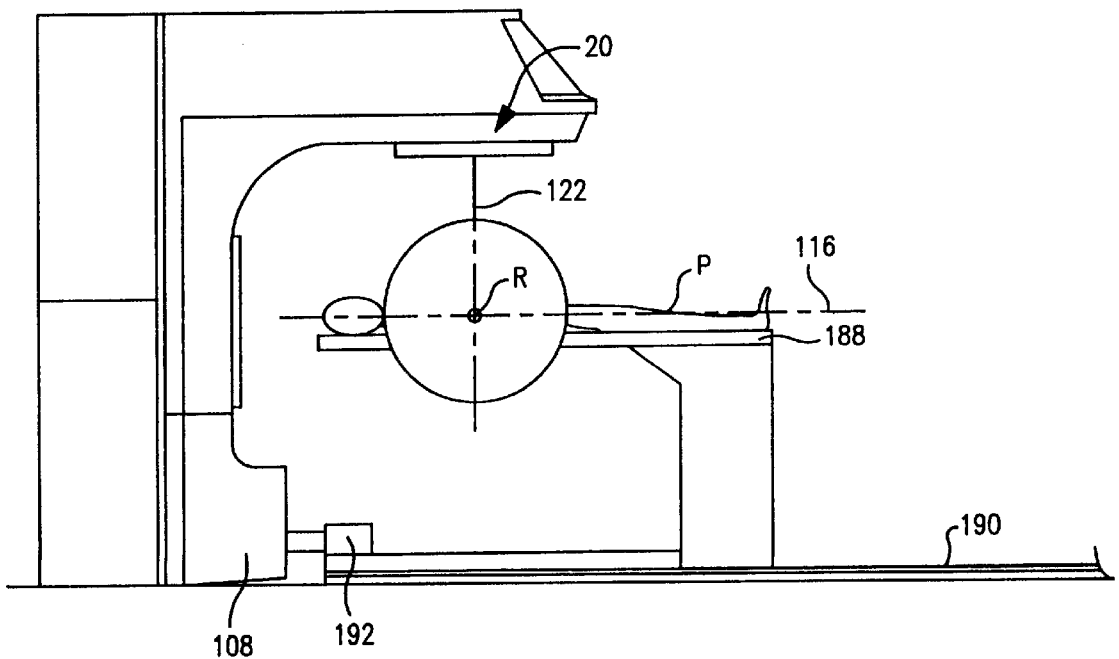
FIG. 11 is a side view of an optional configuration that can be used with the radiotherapy machines and the magnetic resonance imaging system of FIGS. 5 and 6, wherein a treatment couch carrying a subject to be treated by the radiotherapy machine is moved on non-magnetic tracks from one of several waiting positions to an operative position at the radiotherapy machine.
Figure 12:
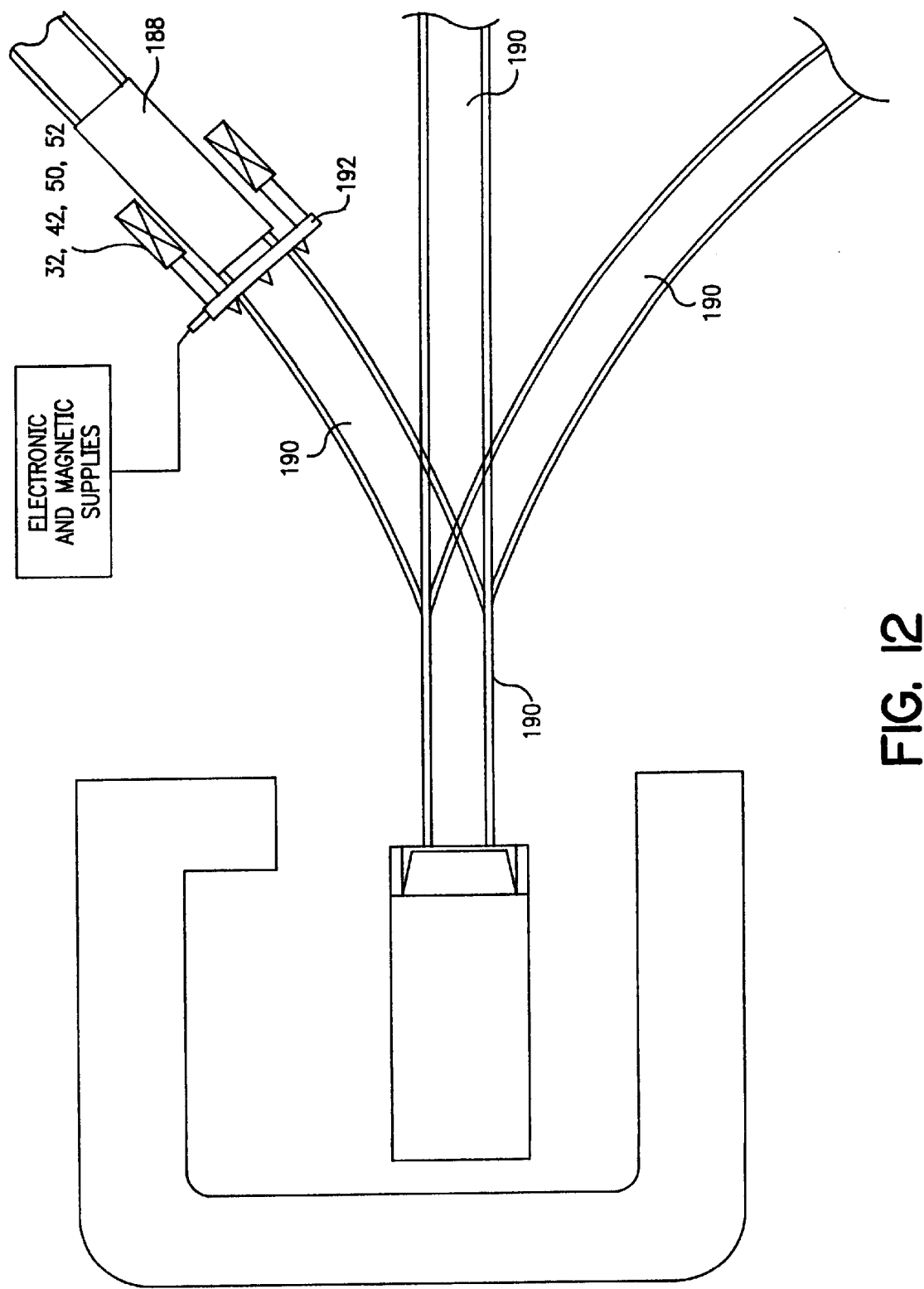
FIG. 12 is a top view of a track assembly to be used with the apparatus illustrated in FIG. 11.

The problem of patient P gaining access to and getting off of the patient bed of radiotherapy machine 20 in a confined magnetically-shielded treatment enclosure because of a close position between the enclosure and the winding segments of coil assembly 32 can be resolved by the apparatus illustrated in FIGS. 11 and 12. In the apparatus of FIGS. 11 and 12, patient P gets on bed 188 at a position remote from radiotherapy machine 20. Coils 32, 42, 50 and 52 of magnetic resonance imaging system 88 are carried by bed 188. After patient P is placed on bed 188 at the remote position, the bed is wheeled into place so that region R desired to be treated is positioned along axis 122 of radiotherapy machine 20. The bed is rolled from a preparation, bed mounting position to the treatment position at the isocenter of machine 20 and system 22. To precisely control the bed position, and, therefore, the position of patient P relative to radiotherapy beam axis 122 and gantry rotation axis 116, bed 188 is rolled along non-magnetic tracks 190. When bed 188 has been rolled into the correct position, the bed is locked onto fixed pedestal 108 of machine 20.

Then electric and mechanical connections are established between pedestal 108 and yoke 192 at the head of bed 188. The mechanical connections lock bed 188 to pedestal 108 and the electrical connections provide power from power supplies in housing 100 to coils 32, 42, 50, 52 and signals from signal sources in housing 100 to motors 31, 33 and 35 as well as to coil 42. Power for imaging and treating is initiated by an operator after region R has been positioned at the intersection of axes 116 and 122 by the operator activating motors 31, 33 and 35.

A single patient bed 188 can shuttle back and forth between a single position external radiotherapy treatment machine 20 or several such beds 188 can shuttle between several external stations and a single treatment machine, as illustrated in FIG. 12. The use of several external positions and several patient beds has the advantage of enabling the treatment machine to have a greater useful cycle time, i.e., a higher duty cycle.

While there have been described and illustrated several specific embodiments of the invention, it will be clear that variations in the details of the embodiments specifically illustrated and described may be made without departing from the true spirit and scope of the invention as defined in the appended claims.

What is claimed:

1. In combination, a radiotherapy machine for deriving a radiotherapy bear for a region of a subject on a treatment couch, and a magnetic resonance imaging system for imaging the region and volumes abutting the region substantially simultaneously with the region being irradiated by the beam, the imaging system including a magnetic excitation coil assembly, the magnetic excitation coil assembly including first and second spaced segments on opposite sides of the region so an axis of the beam is between the first and second segments, the beam being arranged to be propagated along a beam axis, the beam axis being arranged to turn about another axis arranged to approximately extend through the region and approximately intersect the beam axis, the magnetic excitation coil assembly being mounted independently of movement of the beam axis.

2. The combination of claim 1, further including a treatment couch for the subject, the couch including a bed for holding the subject, the bed being movable for enabling the region to be positioned relative to the treatment beam axis.

3. The combination of claim 1, wherein the first and second segments have a common axis substantially coincident with the another axis, the first and second segments deriving main magnetic field lines that extend between the first and second segments in the same general direction as the common axis, a subject holding structure fitting between generally aligned central openings in the first and second segments along the common axis.

4. The combination of claim 1, wherein the first and second segments have a common axis substantially at right angles to the another axis, the first and second segments being arranged so a subject holding structure is between them, the segments producing a main magnetic field having flux lines extending generally in the direction of the common axis.

5. The combination of claim 1, wherein the beam axis and the first and second segments are arranged so the beam axis extends through a space between the first and second segments and generally at right angles to magnetic field flux lines extending between said first and second segments.

6. The combination of claim 1, further including a magnetic shield structure arranged to decouple magnetic fields originating in the radiotherapy machine from magnetic fields originating in the magnetic resonance imaging system.

7. The combination of claim 6, wherein the magnetic shield structure includes: a coil surrounding sources of leakage magnetic fields originating in the radiotherapy machine, and a power source arranged to electrically excite the coil surrounding sources of leakage magnetic fields originating in the radiotherapy machine.

8. The combination of claim 6, wherein the shield structure includes: a coil surrounding sources of leakage magnetic fields originating in the magnetic resonance imaging system, and a power source arranged to electrically excite the coil surrounding sources of magnetic fields originating in the magnetic resonance imaging system.

9. The combination of claim 8, wherein the shield structure includes: a further coil surrounding sources of magnetic fields originating in the radiotherapy machine, and a power source arranged to electrically excite the coil surrounding sources of magnetic fields originating in the radiotherapy machine.

10. The combination of claim 1, wherein the beam is an X-ray beam.

11. The combination of claim 1, wherein the magnetic resonance imaging system includes a coil for deriving a main DC magnetic field, the coil being a non-superconducting wire wound water cooled coil.

12. The combination of claim 1, wherein the magnetic resonance imaging system includes a coil for deriving a main DC magnetic field, the coil being a superconductor.

13. The combination of claim 12, further including a liquid helium source for cooling the superconductor coil to a liquid helium temperature.

14. The combination of claim 13, wherein the coil is a high temperature superconducting coil that is superconducting at temperatures substantially higher than the temperature of liquid helium.

15. The combination of claim 12, wherein the coil is a high temperature superconducting coil that is superconducting at temperatures substantially higher than the temperature of liquid helium, further including a liquid helium source for cooling the superconductor coil to a liquid helium temperature.

16. The combination of claim 1, wherein the magnetic resonance imaging system includes a superconducting rf coil.

17. The combination of claim 1, further including a non-magnetic subject carrying structure, the structure being movable to a first region where the machine is located from a second region outside of the first region and the structure being arranged to be locked in said first region.

18. The combination of claim 17, further including a non-magnetic track at the machine for guiding movement of the structure.

19. The combination of claim 17, wherein the structure carries a coil assembly of the system.

20. The combination of claim 17, further including a plurality of said structures.

21. The combination of claim 1, further including a subject carrying structure, the magnetic excitation coil assembly being positioned to prevent facile access by the subject to and from the structure, a portion of the coil assembly being moveable relative to the structure when the coil assembly is not operative, the coil assembly being moveable to a position facilitating access by the subject to the structure.

22. The combination of claim 21 wherein a coil portion is mounted in a plane extending substantially at right angles to a subject receiving surface of the subject carrying structure, the coil portion being pivotable about an axis extending in the direction of the plane.

23. The combination of claim 21, further comprising motors arranged to control the relative position of the region and the beam by controlling the position of a subject carrying structure relative to an axis of the beam.

24. The combination of claim 1, further comprising a detector responsive to changes in an output of the magnetic resonance imaging system resulting from protons of atoms in the region precessing at a frequency determined by magnetic resonance excitation thereof and subject to de-execution under the influence of radiation products of said beam.

25. In combination, a radiotherapy machine for deriving a radiotherapy beam for a region of a subject on a treatment couch, and a magnetic resonance imaging system for imaging the reaction and volumes abutting the region substantially simultaneously with the region being irradiated by the beam, the imaging system including a magnetic excitation coil assembly, the magnetic excitation coil assembly including first and second spaced segments on opposite sides of the region so an axis of the beam is between the first and second segments, the beam being arrange to be propagated along a beam axis, the beam axis being arranged to turn about another axis arranged to approximately extend through the region and approximately intersect the beam axis, the magnetic excitation coil assembly being mounted so it moves with movement of the beam axis.

26. The combination of claim 25, wherein each of the first and second segments has a central opening including a common axis, the beam axis extending through the central openings of the first and second segments and being generally aligned with the magnetic field flux lines extending between said first and second segments.

27. In combination, a radiotherapy machine for deriving a radiotherapy electron beam for a region of a subject on a treatment couch, and a magnetic resonance imaging system, including a magnetic excitation coil assembly, for imaging the region and volumes abutting the region substantially simultaneously with the reaction being irradiated by the beam, the substantially simultaneous imaging and beam irradiation being each that the radiotherapy electron beam is arranged to be alternately applied to and removed from the region while a magnetic field from the coil assembly is respectively removed from and applied to the region.

28. In combination, a radiotherapy machine for deriving a radiotherapy electron beam for a region of a subject on a treatment couch, and a magnetic resonance imaging system for imaging the region and volumes abutting the region substantially simultaneously with the region being irradiated by the beam, the magnetic resonance imaging system including a superconductor coil for deriving a main DC magnetic field, a liquid helium source for cooling the superconductor coil to a liquid helium temperature, the substantially simultaneous imaging and beam irradiation being such that the radiotherapy electron beam is alternately applied to and removed from the region while current applied to the coil is arranged to be alternately turned off and on, respectively, and further including superconducting leads for applying current pulses to the coil, the superconducting leads being leads having a high superconducting temperature compared to the temperature of liquid helium.

* * * * *